(12) United States Patent
Raub et al.

(10) Patent No.: US 6,589,504 B1
(45) Date of Patent: Jul. 8, 2003

(54) COMPOUNDS AND METHODS FOR DIAGNOSING AND TREATING AMYLOID-RELATED CONDITIONS

(75) Inventors: Thomas J. Raub, Kalamazoo, MI (US); Geri A. Sawada, Portage, MI (US); Steven P. Tanis, Kalamazoo, MI (US); Gregory J. Fici, Kalamazoo, MI (US); Allen Edwin Buhl, Portage, MI (US); Donald Bainbridge Carter, Kalamazoo, MI (US); Tiziano Bandiera, Gambolò-Pavia (IT); Jacqueline Lansen, Milan (IT); Cesare Pellerano, Siena (IT); Luisa Savini, Siena (IT)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/667,357

(22) Filed: Sep. 22, 2000

Related U.S. Application Data

(60) Provisional application No. 60/234,611, filed on Sep. 22, 2000.

(51) Int. Cl.$^7$ ................. A61K 51/00; A61K 49/00; A61M 36/14

(52) U.S. Cl. ............... 424/1.89; 424/1.85; 424/1.81; 424/9.1

(58) Field of Search .............. 424/1.89, 1.85, 424/1.81, 9.1

(56) References Cited

U.S. PATENT DOCUMENTS

| | | | |
|---|---|---|---|
| 3,646,019 A | 2/1972 | Actor et al. | 260/240 |
| 5,731,313 A | 3/1998 | Suarato et al. | 514/255 |
| 5,811,456 A | 9/1998 | Seman et al. | |
| 5,891,909 A | 4/1999 | Soll et al. | |
| 5,955,472 A | 9/1999 | Hays et al. | 514/310 |
| 5,972,956 A | 10/1999 | Hays et al. | 514/297 |
| 5,998,615 A | 12/1999 | Suarato et al. | 544/154 |

FOREIGN PATENT DOCUMENTS

| | | | |
|---|---|---|---|
| EP | 0 503 349 A1 | 6/1992 | |
| EP | 0254776 B1 | 1/1993 | C09J/183/04 |
| EP | 0077956 A1 | 5/1993 | B01J/13/02 |
| WO | WO 94/28412 | 12/1994 | G01N/33/367 |
| WO | WO 96/34853 | 11/1996 | C07C/245/10 |
| WO | WO 97/16191 | 5/1997 | A61K/31/47 |
| WO | WO 97/16194 | 5/1997 | A61K/312/655 |
| WO | WO 97/26919 | 7/1997 | A61K/47/48 |
| WO | WO 97/41856 | 11/1997 | A61K/31/44 |
| WO | WO 97/49433 | 12/1997 | A61K/49/00 |
| WO | WO 98/22146 | 5/1998 | A61K/49/00 |
| WO | WO 98/47969 | 10/1998 | C09B/23/14 |
| WO | WO 99/24394 | 5/1999 | C07C/245/08 |
| WO | WO 00/10614 | 3/2000 | A61K/51/00 |

OTHER PUBLICATIONS

Taya et al, "Complexation Behavior of Heterocyclic Hydrazones" Bull Chem Soc Jpn, vol. 66, No. 12, 1993, pp. 3652–3661.*

Rudolph et al, "2–hydrazino–8–quinolinol and derivatives," J. Med. Chem., 1967, vol. 10, No. 5, p. 981.*

F.H. Case, "Synthesis and Chelation Properties of Hydrazones Derived From Isoquinoline–1–carboxaldehyde, 2–Quinoxalinecarboxaldehyde, 4–Isoquinolylhydrazine, and 2–Quinoxalylhydrazine," Anal. Chem. 1984, 56, pp. 2860–2862.

I.A. Krasavin et al., "2–Formyl–8–hydroxyquinoline Derivatives," Chemistry of Heterocyclic Compounds (English Translation), 1978, pp. 190–194.

T. Rudolph et al., "2–Hydrazino–8–quinolinol and Derivatives," Journal of Medicinal Chemistry, vol. 10, No. 2, Mar. 1967, p. 981.

T. Taya et al., "Complexation Behavior of Heterocyclic Hydrazones. II. Effects of Steric Factors on Formation Constants for Nickel(11) Complexes with Heterocyclic Hydrazones," Bul.Chem. Soc. Jpn., vol. 67, No. 3, pp. 710–719 (1994).

Bartolucci, Cecilia et al.: "Quinolinehydrazones as Inhibitors of Retroviral Reverse Transcriptase," II Farmaco, vol. 47(6), 1992, pp. 945–952.

Berkoff, Charles E. et al.: "Quinolinehydrazones: Structure–Activity Correlations in a New Class of Anti–Mycoplasmal Agents," Arzneim–Forsch. (Drug Res.) vol. 23, Nr. 6, 1973, pp. 830–839.

Dezutter, Nancy A. et al.: "99m Tc–MAMA–chrysamine G, a probe for beta–amyloid protein of Alzheimer's disease," European Journal of Nuclear Medicine, vol. 26, No. 11, Nov. 1999, pp. 1392–1399.

Klunk, William E. et al.: "Chrysamine–G, A Lipophilic Analogue of Congo Red, Inhibits Aβ–Induced Toxicity in PC12 Cells," Life Sciences, vol. 63, No. 20, 1998, pp. 1807–1814.

Klunk, William E. et al.: "Chrysamine–G Binding to Alzheimer and Control brain: Autopsy Study of a New Amyloid Probe," Neurobiology of Aging, vol. 16, No. 4, 1995, pp. 541–548.

Klunk, William E. et al.: "Development of Small Molecule Probes for Beta–Amyloid Protein of Alzheimer's Disease" Neurobiology of Aging, vol. 15, No. 6, 1994, pp. 691–698.

Pellerano, C. et al. "Anticestode Quinolinehydrazones," II Farmaco–Ed.Sc., vol. 30, 1975, pp. 965–973.

(List continued on next page.)

*Primary Examiner*—Sreeni Padmanabhan
*Assistant Examiner*—Michael A. Willis
(74) *Attorney, Agent, or Firm*—Pharmacia & Upjohn; James D. Darnley, Jr.

(57) ABSTRACT

The invention provides methods for diagnosing and treating amyloid-related conditions and compounds useful for the same. The invention provides for detecting, imaging, monitoring, diagnosing, and treating conditions characterized by the binding or aggregation of amyloid fibrils. More particularly, the invention relates to using quinolinehydrazone compounds for diagnosing and treating amyloidotic conditions and also as an antioxidant.

19 Claims, No Drawings

OTHER PUBLICATIONS

Pellerano, C. et al.: "Chinolilidrazoni di Acetilpiridine: Preparazione ed Attivita Biologica," Boll. Chim. Farm., vol. 117, 1978, pp. 721–730. (Text is Italian with English summary at beginning of document).

Pellerano, C. et al.: "Sintesi di Potenziali Agenti Antitumorali: Mostarde Azotate a Supporto Chinolinco," Il Farmaco–Ed.Sc., vol. 39, 1984, pp. 681–685. (Text is Italian with English summary at beginning of document).

Pellerano, C. et al.: "Sopra Alcuni Derivati Idrazinochinolinci: 2–Chinolilidrazoni" Nota VI, Chimica Farmaceutica, Atti. Accad. Fisiocritici Siena, Serie XIV, vol. 8, 1976, pp. 81–93. (Text is Italian with English summary at end of document).

Savini, Luisa et al.: "Chelating Agents as Potential Antitumorals: *–(N)–Heterocyclic Hydrazones and Bis–*–(N)–Heterocyclic Hydrazones," Il Farmaco, vol. 52 (10), 1997, pp. 609–613. Bis–*–(N)–Heterocyclic Hydrazones," Il Farmaco, vol. 52 (10), 1997, pp. 609–613.

Savini, Luisa et al.: "New Quinoline Derivatives: Synthesis and Evaluation for Antiinflammatory and Analgesic Properties—Note II", Il Farmaco, vol. 48, (6), 1993, pp. 805–825.

Sawada, Geri A. et al.: "Increased Lipophilicity and Subsequent Cell Partitioning Decrease Passive Transcelluar Diffusion of Novel, Highly Lipophilic Antioxidants," The Journal of Pharmacology and Experimental Therapeutics, vol. 288, No. 3, 1999, pp. 1317–1326.

Skovronsky, Daniel M. et al.: "In vivo detection of amyloid plaques in a mouse model of Alzheimer's disease," PNAS, vol. 97, No. 13, Jun. 20, 2000, pp. 7609–7614.

* cited by examiner

COMPOUNDS AND METHODS FOR DIAGNOSING AND TREATING AMYLOID-RELATED CONDITIONS

This application claims the benefit of Provisional Application No. 60/234,611, filed Sep. 22, 2000.

BACKGROUND OF THE INVENTION

1. Field of the Invention

The invention provides methods for diagnosing and treating amyloid-related conditions and compounds useful for the same. The invention allows for detecting, imaging, monitoring, diagnosing, and treating conditions characterized by the binding or aggregation of amyloid fibrils. More particularly, the invention relates to the use of quinolinehydrazone compounds for diagnosing and treating amyloidotic conditions.

The invention also encompasses a method for using quinolinehydrazone compounds as an antioxidant.

2. Description of the Related Technology

Disease-causing agents once were believed to be limited to pathogens containing nucleic acids, for example viruses and bacteria. More recently, however, considerable evidence suggests that irregular peptides or proteinaceous infective agents can induce or transmit infectious disease.

Currently, it is widely recognized that some proteins can contain irregular protein sequences which cause living tissue or organs to assemble into insoluble aggregates of partially unfolded proteins, known as amyloid fibrils. All types of amyloid are structurally related by containing Aβ peptides. The Aβ peptides aggregate to form fibrils, which typically have a β-sheet secondary structure. The fibril deposits, or plaque, are believed to be at the root of the pathology for a number of neurodegenerative diseases, or amyloidosis.

In general, the term "amyloidosis" refers to diseases characterized by the tendency of particular proteins to aggregate and precipitate as insoluble fibrils. The fibrils collect in the extracellular space of the surrounding organs or tissues causing structural and functional damage. Common attributes of amyloidosis include, for example, cell toxicity and cell degeneration. For instance, the clinical course of the amyloidotic condition, Alzheimer's disease, is neurodegeneration. Neurodegeneration can be identified, for example, by the progressive loss of mental capacity, loss of motor control, and dementia. Portmortem deposits of amyloid plaque have been identified in patients suffering from Alzheimer's disease, Down syndrome, Type 2 diabetes mellitus, and other amyloid-related conditions.

Infectious protein particles, or prions, also contain irregular protein sequences. These particles typically can be characterized by a single irregular sequence in the protein peptide. The expression of the irregular sequence favors a protein conformation that, like amyloid protein, tends to aggregate. The aggregation of the protein into a plaque has been identified in many patients inflicted with prion disease, such as, for example, Crutzfeld-Jacob disease (CJD), Gerstmann-Straussler-Scheinker syndrome (GSS), fatal familial insomnia (FFI), kuru, Alper's syndrome, scrapie, transmissible mink encepthalopathy (TME), chronic wasting disease (CWD), and bovine spongiform encephalopathy (BSE). In some cases, amyloid plaque has been detected in patients having prion-initiated disease, for example patients diagnosed with CJD. However, prion plaque generally has not been definitively linked to cell impairment. Instead, considerable evidence suggests that the prions propagate by changing the conformation of naturally-existing, non-infectious counterpart proteins into proteins having a harmful secondary structure.

Few methods are known for identifying, treating, or inhibiting the aggregation of amyloid proteins or prions. The target proteins or plaque often exhibit similar properties as healthy, unaffected tissue. As a result, it is difficult to develop an imaging agent selective for only harmful plaque or protein.

Moreover, the harmful plaque often resides in the brain, for example in the case of Alzheimer's disease. To provide a method that is useful for associating with brain plaque, the compound will have useful properties both for binding to amyloid or prion plaque and for crossing the blood-brain barrier. Compounds useful for staining or imaging the plaque in vitro often can not cross the highly discriminant blood-brain barrier to provide a useful in vivo diagnostic or therapeutic tool. Consequently, successful compounds and methods for detecting plaque in vitro can fail as a tool for in vivo imaging.

One compound useful for selectively identifying plaque in vitro is the commercially available diazo dye, Congo red, having the scientific name 3,3'-[[1,1'-biphenyl]-4,4'-diylbis (azo)]bis[4-amino-1-naphthalenesulfonic acid] disodium salt. Congo red has demonstrated binding to amyloid-like proteins with a beta-pleated sheet conformation. See, W. E. Klunk, et al., Quantitative Evaluation of Congo Red Binding to Amyloid-like Proteins with a Beta-Pleated Sheet Conformation, *J. Histochem. Cytochem.*, 37:1273–1281 (1989). However, Congo red lacks the necessary properties to cross the blood-brain barrier as shown by P. D. Griffiths, et al., Receptor Changes in the Neocortex of Postmortem Tissue in Parkinson's Disease and Alzheimer's Disease, *Dementia*, 3:239–246 (1992). As such, the compound provides useful properties for postmortem staining of brain plaque in vitro, but is unsuitable for in vivo use.

Chrysamine G (CG) compounds are a class of compounds derived from Congo red. The predominant structural difference is replacement of sulphonic acid groups in Congo red with carboxylic acid groups. See, for example, International Publication Nos. WO 98/47969, published Oct. 29, 1998; WO 96/34853, published November 7, 1996; and WO 99/24394, published May 20, 1999. In addition, organometallic ligands of Congo red and Chrysamine G compounds have been investigated for use as a diagnostic tool. See, for example, International Publication No. WO 97/41856, published Nov. 13, 1997.

The replacement of sulphonic acid groups with carboxylic acid groups potentially would effect better blood-brain barrier entry of the compound. However, in vivo biodistribution of Chrysamine G compounds has shown that technetium-99m-labeled conjugates of 2-(acetamido)-CG with bis-S-trityl protected monoamide-monoaminedithiol were rapidly cleared from the blood, causing low uptake of the conjugate in the brain. See, for example, N. A. Dezutter, *European Journal of Nuclear Medicine*, Vol. 26,. No. 11, pp. 1392–1399 (1999); W. E. Klunk, et al., *Life Sciences*, Vol. 63, No. 20, pp. 1807–1814 (1998); and W. E. Klunk, et al., Neurobiology of Aging, Vol. 16, No. 4, pp. 541–548 (1995).

Derivatives of 9-acridinone also have been reported as inhibiting amyloid aggregation. International Publication No. WO 97/16191, published May 9, 1997, describes that 9-acridinone compounds inhibit amyloid aggregation in vitro. In vivo diagnostic or therapeutic activity of the compounds is not described.

Commonly-assigned U.S. Pat. Nos. U.S. 5,731,313, and 5,998,615, issued Mar. 24, 1998, and Dec. 7, 1999, respectively, identify fluoroanthracyclinone compounds as useful anti-infective agents and also as a diagnostic agent for imaging amyloid plaque. The in vitro binding of Aβ25–35 peptides is described in International Publication No. WO 97/49433, published Dec. 31, 1997.

More recently, naphthylazo derivatives have been prepared for inhibiting amyloid aggregation. The in vitro binding activity of naphthylazo compounds is described in International Publication No. 97/16194, published May 9, 1997. However, no in vivo data is described in the publication.

Radiolabeled hydrazine and ethylene derivatives of benzenethiazole compounds also have been reported for binding insulin amyloid. See, International Publication WO 97/26919, published Jul. 31, 1997. These compounds show inhibitory activity in vitro, however, to the best of our knowledge, no in vivo activity has been shown.

Of the methods known, the only conclusive test is staining for plaque postmortem. Some compounds have been investigated for in vivo administration and imaging, but it remains beneficial to provide a compound for demonstrating in vitro imaging of compounds.

Accordingly, it remains beneficial to provide a compound for demonstrating in vitro and in vivo imaging of harmful, proteinaceous plaque or infectious agents, more particularly amyloid plaque, prions, or prion plaque. There remains a need to identify compounds and methods for diagnosing and treating conditions related to the aggregation of amyloid or other proteinaceous fibrils. Described here are compounds that provide in vitro imaging, diagnostic opportunities, antioxidant properties and even treatment opportunities for patients suffering from amyloidotic conditions.

SUMMARY OF THE INVENTION

The invention provides diagnostic and therapeutic methods related to detecting, imaging, monitoring, diagnosing, and treating conditions related to aggregation of amyloid or other harmful proteinacious deposits and compounds for accomplishing the methods. Compounds demonstrating beneficial properties for the methods of the invention generally are quinolinehydrazone compounds having the formula:

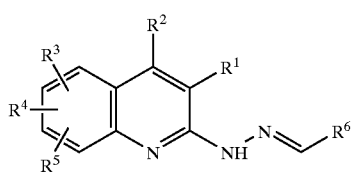

(I)

or a pharmaceutically acceptable salt, ester, solvate or prodrug thereof, wherein:

$R^1, R^2, R^3, R^4$, and $R^5$ are independently selected from the group consisting of hydrogen, alkyl, cycloalkyl, aryl, triflouromethyl, trifluoromethylether, halo, and a group of the formula —$OR^7$, wherein $R^7$ is alkyl or aryl; and $R^6$ is a benzopyridinyl group optionally substituted with one to three substituents selected from the group consisting of hydrogen, alkyl, cycloalkyl, aryl, triflouromethyl, trifluoromethylether, halo, and a group of the formula —$OR^7$, wherein $R^7$ is alkyl or aryl;

wherein said alkyl groups at each occurrence are optionally substituted with alkoxy, aryl, or halo; and said aryl groups at each occurrence are optionally substituted with alkyl, alkoxy, or halo. One or more atoms in the compound can be optionally replaced with a radiolabeled atom, or radioisotope (radioactive isotope). The radioisotope can be selected from the group consisting of $^3H$, $^{131}I$, $^{125}I$, $^{123}I$, $^{76}Br$, $^{75}Br$, $^{18}F$, $^{19}F$, $^{15}O$, and $^{11}C$. Pharmaceutically acceptable salts, esters, solvates, or prodrugs of compounds having the formula (I) can also be suitable for methods of the invention.

In one aspect, therefore, the invention relates to a method for chemically tagging or inhibiting the aggregation of amyloid fibrils comprising administering an effective amount of a compound of formula (I) and allowing the compound to associate with the amyloid fibrils. In this manner, the compound prevents amyloid fibrils from binding to each other and, accordingly, arrests the formation of harmful amyloid plaque.

In another aspect, the invention relates to a method for detecting aggregation of amyloid fibrils. The method comprises (a) administering a compound of formula (I) containing at least one radioactive isotope; (b) allowing the compound to associate with the amyloid fibrils to provide a labeled deposit; and (c) detecting the labeled deposit. The detection method also can be used for monitoring the aggregation of amyloid fibrils in an individual. If necessary or appropriate, data obtained from detecting the labeled amyloid deposit, such as the location and the amount of amyloid deposit, can be recorded to allow one with skill in the art to assess the status and/or progress of the amyloidotic condition.

The method also can be used for identifying or diagnosing a condition characterized by aggregation of amyloid fibrils, further comprising evaluating or assessing the amount and placement of the radioactive isotope to determine the medical condition of the individual, or patient. To achieve the full advantage of the invention, the data can be evaluated or assessed in light of data obtained from a normal, i.e. free of amyloid-plaque, individual. In this aspect, the method comprises identifying or using a biomarker for conditions characterized by the aggregation of amyloid fibrils. In addition, the method can also be used in a patient undergoing treatment for a condition characterized by the aggregation of amyloid fibrils to evaluate the progress of the course of treatment.

In another aspect, the invention relates to a method for treating a condition characterized by aggregation of amyloid fibrils comprising administering a compound of formula (I), optionally in a pharmaceutically acceptable carrier, and allowing the compound to associate with the amyloid plaque. The treatment can be carried out by allowing the compound to directly bind to or inhibit the aggregation of the amyloid plaque. The steps of administering the compound and allowing it to associate can be repeated as necessary or desired to effectuate treatment of the amyloid-related condition.

Alternatively, the compound can deliver therapeutic agents to the amyloid fibrils. The method for delivering a treatment for a condition characterized by aggregation of amyloid fibrils, therefore comprises (a) providing a compound of formula (I) in combination with a therapeutic agent; (b) administering the combination to an individual having amyloidosis; and (c) optionally repeating steps (a) and (b), as necessary, to improve or rehabilitate the condition of the individual.

Yet another aspect of the invention relates to a method for staining amyloid fibrils comprising (a) applying a compound of formula (I) to a sample containing amyloid fibrils to form a labeled deposit and (b) detecting the labeled deposit.

In addition, the invention can relate to a method for detecting amyloid deposits in biopsy or postmortem human or animal tissue comprising the steps of (a) incubating formalin-fixed tissue with a solution of a compound of formula (I) to form a labeled deposit and (b) detecting the labeled deposit.

The compounds also can be contacted with bodily fluids extracted from a mammal to detect aggregated prion proteins. In this aspect, a bodily fluid is extracted from the mammal and contacted with the bodily fluid of a compound of formula (I).

In yet another aspect, a quinolinehydrazone compound can be used as an antioxidant by administering the compound, optionally in a pharmaceutically acceptable carrier. The quinolinehydrazone compound can comprise a compound of formula (I).

Yet another aspect of the invention relates to a complex comprising a compound of formula (I) in association with or bound to an amyloid fibril. The complex also can comprise a compound of formula (I) in association with or bound to a proteinaceous infectious particle, or prion.

DETAILED DESCRIPTION OF THE INVENTION

Quinolinehydrazone compounds possess beneficial properties for providing novel diagnostic and therapeutic methods for detecting, imaging, monitoring, diagnosing, and treating conditions related to aggregation of amyloid and other harmful proteinacious deposits. Preferred quinolinehydrazone compounds comprise:

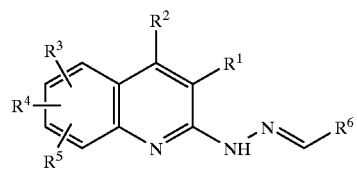

(I)

or a pharmaceutically acceptable salt, ester, solvate, or prodrug thereof, wherein $R^1$, $R^2$, $R^3$, $R^4$, $R^5$, and $R^6$ are as previously defined, and wherein one or more atoms of the compound optionally can be substituted with a radiolabeled atom.

The term "alkyl" as used herein refers to a straight or branched hydrocarbon group, preferably containing one to six carbon atoms. Examples of useful alkyl groups include, but are not limited to, methyl, ethyl, n-propyl, sopropyl, n-butyl, sec-butyl (1-methylpropyl); t-butyl (1,1-dimethylethyl), n-pentyl, t-pentyl (1,1-dimethylpropyl), n-hexyl, and the like. Alkyl groups for the invention also can include groups wherein the hydrocarbon contains one or more substituents such as, for example, cycloalkyl, alkoxy, aryl, or halo as defined hereinbelow. The substituents can bond with the same carbon or different carbons. Typically, the hydrocarbon contains one, two or three substituents, if any.

The term "alkoxy" as used herein refers to a straight or branched hydrocarbon group as defined above attached to the parent molecule through an oxygen heteroatom, typically by a carbon to oxygen bond. The hydrocarbon of the alkoxy group preferably contains from 1 to 6 carbon atoms. Typical alkoxy groups are methoxy, ethoxy, n-propbxy, isopropbxy, n-butoxy, sec-butoxy (1-methylpropoxy), t-butoxy (1,1-dimethylethoxy), n-pentoxy, t-pentoxy (1,1-dimethylpropoxy), and the like.

The term "cycloalkyl" as used herein refers to nonaromatic cyclic hydrocarbon group, preferably containing from three to six carbon atoms. Examples of cycloalkyl are cyclopropyl, cyclobutyl, cyclopentyl, cyclohexyl, and the like. Cycloalkyl groups may be substituted with alkyl and alkoxy groups, as defined above, as well as halo substituents, for example, bromo, chloro, iodo, and fluoro.

The term "aryl" as used herein refers to an aromatic cyclic hydrocarbon, such as phenyl and naphthyl. The aryl group optionally can be substituted with alkyl, alkoxy or a halo group, for example, bromo, chloro, iodo, and fluoro. Examples of aryl groups include, but are not limited to, phenyl, bromophenyl, chlorophenyl, iodophenyl, fluorophenyl, bromonaphthyl, and the like.

The term "triflouromethyl" as used herein refers to a methyl group ($—CH_3$) wherein each hydrogen atom is substituted with a fluorine atom. Similarly, "trifluoromethylether" is a trifluoromethyl group, as defined above, linked to the parent molecule through an oxygen heteroatom, typically by a carbon-oxygen bond. The trifluoromethyl and trifluoromethylether groups can be represented by the formulae $—CF$, and $—OCF_3$, respectively.

The term "halo" as used herein refers to a monovalent substituent derived from a halogen. Typical halogens are, for example, bromine, chlorine, iodine, fluorine, and the like.

The term "benzopyridinyl" as used herein refers to a group derived from a compound comprising a fused benzene and pyridine ring, generally called a benzopyridine. Examples of benzopyridine compounds are quinoline and isoquinoline. The corresponding groups derived from quinoline and isoquinoline are quinolyl and isoquinolyl, respectively. The benzopyridinyl groups can contain one or more substituents, typically selected from alkyl, aryl, triflouromethyl, trifluoromethylether, halo, and a group of the formula $—OR^7$, wherein $R^7$ is alkyl or aryl.

The term "radiolabeled atom", "radioisotope", or "radioactive isotope" as used herein refers to an atom, which can be incorporated into a compound, capable of emitting waves or particles of radioactive energy, typically light and/or heat. More particularly, the atoms decay from a radioactive atom to a naturally occurring atom containing the same number of protons by emitting electrons. Examples of radiolabeled atoms or radioisotopes are $^3H$, $^{131}I$, $^{125}I$, $^{123}I$, $^{76}Br$, $^{75}Br$, $^{18}F$, $^{19}F$, $^{15}O$, and $^{11}C$.

It has now been discovered that quinolinehydrazone compounds, particularly quinoline- or isoquinoline-substituted quinolinehydrazone compounds, exhibit antioxidant properties and can bind to amyloid fibrils, inhibiting the aggregation thereof. The compounds demonstrate in vitro activity for inhibiting seeded aggregation of amyloid fibrils as well as demonstrate in vitro antioxidant properties in oxidative neuronal models. Moreover, the compounds can cross the blood-brain barrier in vivo to provide a beneficial diagnostic or therapeutic tool.

Certain quinolinehydrazone compounds previously have described as antimicrobial, antiparasitic, anti-mycoplasmal, and anti-HIV agents. See; for example, *Atti Accad. Fisiocritici Siena*, Serie XIV, Vol. 8, 82–93 (1976); *Arzneim.-Forson.* (*Drug Res.*) 23, Nr. 6, 830–839 (1973); *Il Farmaco*, 47(6), 945–962 (1992); and U.S. Pat. No. 3,646,019. However, quinolinehydrazone compounds reported in the literature typically are substituted with monocyclic, if any, heteroaryl groups. There is no known description of using quinolinehydrazine compounds for binding to amyloid fibrils or inhibiting the aggregation of such fibrils either in vitro or in vivo. In addition, quinoline- and isoquinoline-substituted quinolinehydrazone compounds have not been described as a compound per se, either for demonstrating therapeutic activities or as a diagnostic tool.

The compounds can be prepared by any suitable process. The compounds can be prepared from 2-hydrazinochloroquinoline starting materials or, in the alternative, prepared by reacting the corresponding 2-chloroquinoline with hydrazine hydrate. The 2-hydrazinoquinoline group is reacted with the carboxaldehyde of the desired benzopyridyl substituent, for example 4-quinolinecarboxaldehyde. The reaction is preferably carried out in an organic solvent, typically alcoholic solvents, for example, methanol, ethanol, isopropanol, and the like. The most preferred organic solvent is ethanol. To facilitate preparation, the compounds. can be reacted in the presence of heat, typically from about 50–70° C. Additional discussion of the methods, reagents and conditions for preparing the quinolinehydrazone derivatives, in general, are described in *Atti Accad. Fisiocritici Siena*, Serie XIV, Vol. 8, 82–93 (1976); *Arzneim.-Forson.* (*Drug Res.*) 23, Nr. 6, 830–839 (1973); *Il Farmaco*, 47(6), 945–962 (1992).

Radiolabeled compounds can be prepared by reacting a compound of formula (I) with a radioactive isotope or a suitable reagent containing the isotope. A thorough discussion regarding methods for preparing radiolabeled compounds and derivatives is provided in Kirk-Othmer, *Encyclopedia of Chemical Technology*, 4th ed., vol. 20, John Wiley & Sons, Inc., New York, N.Y. (1999), and more particularly in pp. 930–962.

A compound of formula (I) can bind to Aβ peptide sequences with a dissociation constant (Kp) between 0.001 and 10.0 μM when measured by binding to synthetic Aβ peptide or to amyloid fibrils in brain tissue. In addition, the compound is capable of traversing capillary endothelial cells with continuous junctions and no detectable transendothelial pathways to reach the brain, commonly called the blood-brain barrier, which is beneficial for a diagnostic tool if used in the brain. Dose-dependent concentrations of the compound can be detected in the brain and plasma of C57 female mice when administered in vivo, which indicates transport across the blood-brain barrier.

Preferred compounds for the methods of the invention can be represented by the general formula (I), or can comprise a salt, ester, solvate, or prodrug thereof, having at least one atom of the original parent compound replaced with a radioactive isotope. The radioactive isotopes emit wave frequencies, which are typically readily detectable by a variety of detectors or imagers. The scope of the invention contemplates detectors and imagers primarily functioning on the detection of wave frequencies, for example photon emissions, positron emissions, gamma emissions, and the like. The detector and imaging apparatus suitable for use with the invention is not limited by commercial availability of the units, however, many practical units for detecting, imaging, possibly in combination with recording, the presence of the radioactive isotopes in the body of the mammal are readily available. More particularly, non-invasive units for detecting and imaging radioactive isotopes in vivo, generally in combination with electronic, photographic, or textual methods of recording data, are also contemplated. The detector or imaging equipment detect wave frequencies emitted from the labeled compounds that can be distinguished from other non-labeled compounds, i.e. compounds not containing a radioactive isotope. It is well within the purview of one skilled in the art to determine the particular radioactive isotope for an intended detection or imaging assay, considering the frequency range and sensitivity of the detector, the chemical and physical properties of the imaging agent, and other factors relevant to the precision, accuracy, and validity of the assay.

The preferred substituents for $R^1$, $R^2$, $R^3$, $R^4$, and $R^5$ are each independently selected from hydrogen, methyl, ethyl, n-propyl, isopropyl, n-butyl, sec-butyl, t-butyl, n-pentyl, t-pentyl, n-hexyl, methoxy, ethoxy, isopropoxy, sec-butoxy; t-butoxy, phenyl, benzyl, trifluoromethyl, trifluoromethylether, or halo. The preferred group for the substituent $R^6$ in a compound of formula (I) is quinolyl or isoquinolyl. More preferred compounds for the methods of the invention have the formula:

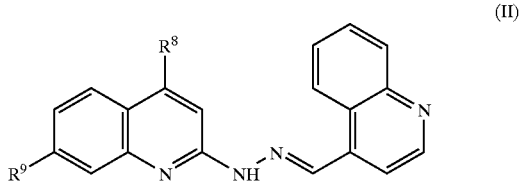

(II)

wherein $R^8$ and $R^9$ are as previously defined for the substituents $R^1$, $R^2$, $R^3$, $R^4$, and $R^5$, or a pharmaceutically acceptable salt, ester, solvate, or prodrug thereof. The more preferred substituents for $R^8$ and $R^9$ are each independently selected from hydrogen, methyl, ethyl, n-propyl, isopropyl, n-butyl, sec-butyl, t-butyl, n-pentyl, t-pentyl, n-hexyl, methoxy, ethoxy, isopropoxy, sec-butoxy, t-butoxy, phenyl, benzyl, trifluoromethyl, trifluoromethylether, or halo. Preferred radiolabeled atoms are $^3H$, and $^{125}I$.

More particularly, the more preferred compounds for the invention include, but are not limited to:

4-methyl-7-methoxy-2-(4-quinolylmethylenehydrazino) quinoline;

4-ethyl-7-methoxy-2-(4-quinolylmethylenehydrazino) quinoline;

4-ethyl-7-ethoxy-2-(4-quinolylmethylenehydrazino) quinoline;

4-methyl-7-ethoxy-2-(4-quinolylmethylenehydrazino) quinoline;

4-ethyl-7-ethoxy-2-(3-quinolylmethylenehydrazino) quinoline;

4-ethyl-7-methoxy-2-(3-quinolylmethylenehydrazino) quinoline; and 4-methyl-7-methoxy-2-(3-quinolylmethylenehydrazino) quinoline.

The term "pharmaceutically acceptable salt, ester, solvate, or prodrug thereof" refers to derivatives prepared from a parent compound, in this case the quinolinehydrazone compound. The salts include, but are not limited to, alkali metal salts, alkaline earth metal salts, ammonium salts, salts with an appropriate organic amine or amino acid, and acid addition salts prepared with organic or inorganic acids such as, for example, hydrochloric acid, sulfuric acid, carboxylic acid, and sulfonic acids. Esters more particularly refer to condensation products of the parent compound with an organic acid, for example, acetate, propionate, butyrate, valerate, benzoate, salicylate, succinate, and the like. Solvates refer to'ionic or molecular complexes comprising the parent compound and one or more molecules of solute, typically an organic solvent, and preferably water. Prodrugs are obtained in vivo when a chemical compound is converted into a parent compound,!.for example a quinoline- or isoquinoline-substituted quinolinehydrazone, by natural metabolic processes of the body.

When administered to a mammal, the compounds have demonstrated an ability to interact with amyloid fibrils, and particularly with amyloid fibrils in the brain. To achieve the full advantage of the invention, the compound is allowed to interact with the amyloid fibrils, generally by allowing a sufficient time for bonding, associating, conjugating, complexing, or other reaction to take place. In the presence of amyloid fibrils, the labeled compounds interact with the amyloid fibrils to form a labeled amyloid fibril complex. In particular, the radiolabeled compound can be used to bind to brain amyloid fibrils including, for example, protofibrils, type-1 fibrils, type-2 fibrils, neuritic plaque, diffuse amyloid, and combinations thereof. In some cases, the compound may interact with only one type of fibril, either by nature or by design. In a preferred case, the compound specifically interacts with β-amyloid protofibrils and, more specifically, β-amyloid protofibrils in the brain.

For the convenience and ease of administration, the compound commonly is prepared into a pharmaceutical composition. In a typical pharmaceutical composition, a quinolinehydrazone compound or a derivative thereof, including a radiolabeled compound prepared therefrom, as described above, is combined with a pharmaceutically acceptable carrier. The carrier can comprise one or more solubilizing agents, excipients, additives, diluents, or other agents to improve the characteristics of the composition. In general, the compound is formulated with the carrier in any manner suitable for providing a pharmaceutical dosage form, typically resulting in a sterile, non-toxic mixture or blend of the active agent with a carrier. The composition can be administered orally, parenterally, subcutaneously, intravenously, intramuscularly, intracisternally, or by infusion techniques. Methods for preparing pharmaceutical compositions are readily available in the art and are further described, for example, in *Remington: The Science and Practice of Pharmacy*, Nineteenth Edition, vol. II, Mack Publishing Company, Easton, Pa., 1995, in particular with respect to solutions, emulsions, suspensions, and extracts on pp. 1485–1533; intravenous admixtures on pp. 1542–1562; oral dosage forms on pp. 1615–1649; sustained-release delivery systems on pp. 1660–1675; and aerosols on pp. 1676–1692.

In particular, the compounds can be administered in a liquid, solid, or semi-solid oral dosage form. Examples of common dosage forms suitable for the invention are tablets, capsules, troches, lozenges, emulsions, solutions, tinctures, syrups, elixirs, and the like. Oral dosage forms can optionally contain one or more chemically non-reactive excipients, for example, sweetening agents, flavoring agents, coloring agents, preserving agents, and the like.

The active agent can be admixed with excipients, such as inert diluents, granulating and disintegrating agents, binding agents, and lubricating agents to provide a suitable tablet. Examples of inert diluents suitable for the tablet are, for example, calcium carbonate, sodium carbonate, lactose, calcium phosphate and sodium phosphate. Granulating and disintegrating agents suitable for the invention include, but are not limited to, maize starch, alginic acid, and the like. Binding agents, for example maize starch, gelatin or acacia, can also be incorporated into the tablet. Lubricating agents, such as, for example magnesium stearate, stearic acid or talc, are also suitable for the invention.

The tablets can be optionally coated by a wide variety of techniques to facilitate administration, improve taste, provide a sustained action over a longer period, or delay disintegration or adsorption in the gastrointestinal tract. For example, a time delay material such as glyceryl monostearate or glyceryl distearate may be employed. Techniques for coating tablets, in general, are further described in Coating of Pharmaceutical Dosage Forms by Stuart C. Porter, reprinted in *Remington: The Science and Practice of Pharmacy, Nineteenth Edition*, vol. II, Mack Publishing Company, Easton, Pa., 1995, in particular in pp. 1650–1659.

Capsules are another dosage form suitable for oral administration. The term "capsules" is intended to include hard capsules, soft capsules such as gel capsules, microcapsules, and the like. The active ingredient can be mixed with an inert solid diluent, for example, calcium carbonate, calcium phosphate or kaolin, or a soft gelatin capsule wherein the active ingredient is mixed with water or an oil medium, for example, peanut oil, liquid paraffin, or olive oil.

Aqueous suspensions can contain the active materials in admixture with one or more compatible excipients. Such excipients are suspending agents, for example, sodium carboxymethylcellulose, methylcellulose, hydroxymethylcellulose, hydroxypropylmethylcellulose, sodium alginate polyvinylpyrrolidone, gum tragacanth and gum acacia; dispersing or wetting agents such as naturally-occurring phosphatides, for example lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and a hexitol anhydrides, for example polyoxyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

In addition to aqueous suspensions, the active agent can be formulated as an.oily suspension. The oily formulation is prepared by suspending the active ingredient in a vegetable oil, for example arachis oil, olive oil, sesame oil, coconut oil, or mineral oil, such as liquid paraffin. The oily suspensions may contain a thickening agent for example beeswax, hard paraffin or cetyl alcohol. Sweetening agents, such as those set forth above and flavoring agents may be added to provide a palatable oral preparation. These compositions may be perserved by the addition of an antioxidant, such as ascorbic acid. Dispersible powders and granules are also suitable for the oily suspension. The powders and granules can be incorporated into the suspension with dispersing or wetting agents, suspending agents and one or more preservatives. Suitable dispersing or wetting agents and suspending agents are exemplified by those already mentioned above for the aqueous suspension. Additional excipients, for example sweetening agents or flavoring agents, may also be present.

The pharmaceutical composition can also be oil-in-water emulsions. The oily phase of the emulsion can be an oil selected from vegetable oil, for example, olive oil or arachis oil; a mineral oil, for example, liquid paraffin; or a combination thereof. The emulsifying agents can be naturally-occurring gums, phosphatides, esters or partial esters derived from fatty acids and hexitol anhydrides, and condensation products of said partial esters. Suitable emulsifying agents are gum acacia, gum tragacanth, soybean oil, lecithin, sorbitan monooleate, polyoxyethylene sorbitan monooleate. The emulsion can also contain sweetening and flavoring agents including, in addition, syrups and elixirs such as glycerol, sorbitol, or sucrose, for example. Such formulation can also contain soothing agents (demulcents), preservatives, flavoring agents, and coloring agents.

Aqueous and oily suspensions described for the oral dosage forms can be formulated into parenteral dosage, for example subcutaneously, intravenously, intramuscularly, intracisternally, or by infusion. The suspensions can be formulated using one or more non-toxic parenterally acceptable diluents or excipients. Excipients suitable for the invention include dispersing agents, wetting agents, suspending agents, and the like. The suspension can be incorporated into a solvent vehicle, for example 1,3-butane diol, water, Ringer's solution, isotonic sodium chloride solution, and the like. In addition, sterile, fixed oils are also suitably employed as a solvent or suspending medium. Examples of oils for the parenteral composition are monoglycerides, diglycerides, and fatty acids, for example oleic acid.

Amyloid fibrils can be present anywhere in the body of the mammal. Typically, amyloid fibrils aggregate in a particular organ, or part of the organ, and form a film or mass of amyloid fibrils, called amyloid plaque. Amyloid fibrils and amyloid plaque can be found, for example, in the brain, pancreas, vasculature, spleen, liver, kidneys, adrenals, lymph nodes, muscle, cardiovascular system, skin, or any combination thereof.

A significant advantage of the invention is the assessment of the amyloid fibrils localization and the ability to quantify the labeled amyloid fibrils. The localization or quantification of the labeled amyloid fibrils can be determined a variety of techniques. Examples are radioimaging, magnetic resonance imaging (MRI), single photon emission computed tomographic imaging (SPECT), and other suitable detection or imaging techniques.

Overproduction of the readily aggregating amyloid protein can cause numerous disease including, but not limited to, Alzheimer's disease, Down syndrome, Type 2 diabetes mellitus, amyloid A (reactive), secondary amyloidosis, familial mediterranean fever, procalcitonin, Cruetzfeld-Jacob disease, bovine spongiform encephalitis, and the like. Moreover, mutations in the pathogenic genes believed to cause disease, for example, presenilin and APP genes, have been shown to cause an increase in amyloid aggregation. Accordingly, the detection.of amyloid aggregation, or the resulting amyloid plaque, is indicative of amyloid-related pathogenic disease.

In accordance with the method of diagnosing a person having a condition associated with aggregated amyloid, the data is recorded and assessed by one with skill in the art of diagnosing or treating amyloid-related disease. The method can be used for a wide variety of amyloid-related disorders including, for example, but not limited to, Alzheimer's disease, Down syndrome, Type 2 diabetes mellitus, hereditary cerebral hemorrhage amyloidosis, amyloid A, secondary amyloidosis, familial mediterranean fever, familial amyloid nephropathy with urticaria and deafness, amyloid lambda L-chain or amyloid kappa L-chain, A beta 2M, ATTR, familial amyloid cardiomyopathy, isolated cardiac amyloid, AIAPP or amylin insulinoa, atrial naturetic factor, procalcitonin, gelsolin, crytatin C, AApo-A-I, AApo-A-II, fibrinogen-associated amyloid; and Asor or Pr P-27 or in cases of persons who are homozygous for the apolipoprotein E4 allele, and the condition associated with homozygosity for the apolipoprotein E4 allele. More particular examples of such diseases include, but are not limited to, Dutch hereditary cerebral hemorrhage amyloidosis amyloid A, Muckle-wells syndrome, idiopathic-associated amyloid lambda L-chain, myeloma-associated amyloid lambda L-chain, macroglobulinemia-associated amyloid lambda L-chain, idiopathic-associated amyloid kappa L-chain,; myeloma-associated amyloid kappa L-chain, macroglbbulinemia-associated amyloid kappa L-chain, Portuguese familial amyloid polyneuropathy, Japanese familial amyloid polyneuropathy, Swedish familial amyloid polyneuropathy, Danish familial amyloid cardiomyppathy, systemic senile amyloidosises, isolated atrial amyloid, medullary carcinoma of the thyroid, Finnish familial amyloidosis, Icelandic hereditary cerebral hemorrhage with amyloidosis, scrapie, Cruetzfeld-Jacob disease, Gertsmann-Straussler-Scheinker syndrome, and bovine spongiform encephalitis.

In some cases, the data obtained regarding the localization and quantification of the labeled amyloid fibrils can be compared to a standard, such as, for example, the localization and quantification patterns of a mammal having normal, or typical, levels of amyloid plaque relative to like species. In accordance with a method of monitoring the aggregation of amyloid fibrils, the data obtained from the detection or imaging methods can be compared with earlier assessments of the amyloid condition in the mammal as well as comparing the method to a standard to determine the state of the amyloid aggregation or the progression of the disease.

The data obtained also can be used in conjunction with a single dose or a regimen of therapy to determine the effect of the therapy on the localization or quantification of the amyloid fibrils. For example, the radiolabeled compound can be administered to a patient undergoing a course of amyloid-affecting therapy, such as doxorubicin, an organic molecule. The radiolabeled compound interacts with the amyloid fibrils to provide an amyloid-labeled complex, which can be used to detect, image, and preferably record, the condition of the affected organ at desired periods in the therapy. The state of the amyloid aggregation and the progress of the therapy can be suitably monitored.

In another example, the radiolabeled compound is administered to a mammal suspected of having an amyloid-related disorder. The radiolabeled amyloid fibril complex is detected or imaged by the described methods to obtain localization patterns and quantification of the labeled amyloid fibrils. The data obtained regarding the state of the amyloid aggregation can be recorded and compared with data obtained from a normal, i.e. disease-free, brain to determine the state of amyloid-affectedness in the patient. In this aspect, the radioactive compound can be used as a biomarker for determining the relative condition of a mammal potentially suffering from an amyloid-related disorder.

The preferred formulation for the compound is an oral dose form. More preferably, the compound is administered as a suspension, solution, or tincture. Dosage levels of the compound can be determined by one with skill in the art, considering the age, weight, and condition of the subject to be treated, as well as the severity of the disease, the frequency of the desired dosing, and the route of administration. In particular, the compound can be prepared in a single dose formulation for the detection and imaging aspects of the invention. To provide guidance to the reader in carrying out the practice of the invention, an oral dose in the range of from about 10 to about 1000 milligrams per kilograms of body weight per day (mg/kg/day) are suitable for the invention. The preferred dosage for the detection and imaging aspects of the invention are from about 250 to about 750 milligrams per kilograms of body weight per day.

A method of the invention can also relate to treating a condition characterized by aggregated amyloid fibrils. In this aspect, a therapeutically effective amount of a compound of formula (I) is administered to the mammal, typically in a pharmaceutical carrier. A sufficient amount of time is allowed for the compound to interact with amyloid fibrils in the body. The interaction between the compound and the amyloid fibrils inhibits amyloid protein fibrils from aggregating and forming amyloid plaque. A "therapeutically effective" amount is the amount of active agent sufficient to inhibit or treat the condition.

The compounds also can be used to deliver treatment for an amyloid-related condition. The compound can be bound to a therapeutic treatment, typically a drug therapy, for example, synthetic or naturally-derived organic compounds, proteins, antibodies, and the like.

The compound, in combination with the therapeutic treatment, are administered to a mammal, particularly a mammal in need of treatment for an amyloid-related condition. The compound interacts with the amyloid fibrils, transporting the target treatment to the site where the treatment is needed. The compounds have demonstrated an affinity for the amyloid fibrils and, accordingly, deliver the desired treatment efficiently and effectively to the target area, i.e. where the amyloid fibrils aggregate. Examples of active agents that can be monitored include, but are not limited to, specific and non-specific drug treatments such as proteins, peptides, carbohydrates, polysaccharides, glycoproteins, nucleic acids, antibodies, peptidomimetics, organic molecules (preferably, less than 1500 kDa), fragments or recombinant forms of the above; inhibitors or activators of a molecule that is required for inhibiting, synthesizing, post-translation modification of, or functioning of some element involved in the localization or quantification of amyloid; regulators in the spatial or temporal control of expression of a gene product; cytokines, growth factors, hormones, signaling components, kinases, phosphatases, homeobox proteins, transcription factors, translation factors, post-translational factors and enzymes. Broad categories of drug therapies include, but are not limited to, cholinesterase inhibitors, muscarinic agonists, anti-oxidants or anti-inflammatory agents. Examples of active agents for amyloid-related disorders are doxorubicin, galantamine, tacrine (COGNEX®), selegiline, physostigmine, revistigmin, donepizil (ARICEPT®), metrifonate, milameline, xanomeline, saeluzole, acetyl-L-carnitine, idebenone, ENA-713, memric, quetiapine, neurestrol and neuromidal.

In addition to methods for treating amyloidosis, the compounds also have demonstrated activity as an antioxidant. To enjoy the antioxidant properties of the invention, a quinolinehydrazone compound, for example a compound of formula (I), is administered to a patient, preferably in a pharmaceutically acceptable carrier as previously described. The antioxidant properties of the compound are especially beneficial for treating conditions characterized by oxidative damage in the body, for example oxidative neuronal damage. Preferably, the compound is administered as an oral or intravenous dosage form.

Dosing for the compound as a treatment agent, either for treating amyloidosis or for treating a condition characterized by oxidative damage, can be administered in any suitable manner. Examples of dosing regimens suitable for the invention are orally, parenterally, subcutaneously, intravenously, intramuscularly, intracisternally, or by infusion, as described for the diagnostic aspect of the invention. The prescribed dosing can be administered within the reasonable medicament judgment of the professional treating the patient, however, it is suggested that a suitable dose of the compound is in the range of from about 10 to about 1000 milligrams per kilograms of body weight per day.

The invention also relates to a method for detecting the presence of aggregated prion protein in a mammal. The compound can be administered orally as with the aspect of the invention related to amyloid-related detection and imaging. Prions, however, are more common in animals. As such, it is preferred with the aspect of the invention related to prion detection that a body fluid or tissue from the subject mammal is obtained. The fluid or tissue is allowed to interact with the compound to identify the presence of any aggregated prion. The presence of the aggregated prion can be determined by the detection and imaging techniques previously described. In this manner, the invention can be more efficiently and effectively carried out for the practice of detecting and imaging the presence of aggregated prion in animals. Examples of prion-related disease, in particular, are generally diseases that affect livestock including, but not limited to, scrapie, a disease common to sheep, and bovine spongiform encephalopathy (BSE), which typically affects cows and is more commonly known as mad cow disease.

As previously mentioned, human prion is less common than animal prion. Human prion has been reported in elderly patients and is believed to be transmitted to humans via BSE-infected beef. Accordingly, the quinolinehydrazone compounds can also be used to identify prion aggregation in humans.

Any body fluid extracted from the subject can be used for the assay. Typically, bodily fluid is meant to refer to fluids such as, for example, lymph, blood, or urine. The preferred bodily fluid is lymph. In certain preferred embodiments, the bodily fluid is filtered in vitro such that any prion infectious agent present in the bodily fluid does not pass through the filter. For example, a Millipore Ultrafree-MC polysulfone membrane, 3000,0000 NMWL cutoff, can be used. The filter is contacted with the compound. The presence of the resulting labeled prion protein is determined using a SPECT detector, though any other method known to those skilled in the art to detect the labeled prion can also be used.

In another aspect, the invention relates to a complex comprising a compound of formula (I) in association with or bound to the amyloid fibril or prion particle. As previously described amyloid fibril and prion particles have demonstrated properties indicative of or causing disorders such as Alzheimer's and Crutzfeld-Jacob syndrome. By providing a compound of formula (I) and allowing the compound to associate with an amyloid fibril or prion, a complex of the compound with the amyloid fibril or prion is formed. The complex is useful for the identification of the amyloid fibril or prion. For example, the complex can include a radiolabeled compound, which can be identified with a suitable detection method.

The invention can be better understood in light of the following examples which are intended as an illustration of the practice of the invention and are not meant to limit the scope of the invention in any way.

EXAMPLE 1

Determination of in vivo Brain Distribution: Intravenous Dosing

Transgenic mice, designated "Tg", were obtained. The transgenic mice carry the human gene for β-APP, a gene associated with β-amyloid deposition in the brain. The mice were treated with.the quinolinehydrazone compound, 4-methyl-7-methoxy-2-(4-quinolylmethylhydrazino) quinoline. Dosing was administered either intravenously or orally. The intravenous dose was administered as a single injection (50 μmol/kg). Orally-treated animals received a single dose (400 μmol/kg) via oral gavage, or were dosed twice-a-day for 10 days (400 μmol/kg/dose/day).

Age-matched normal mice served as a negative control, i.e. no plaque formation in the animals was indicated. The control mice were treated in the same manner as the transgenic mice, but with placebo.

In addition, a group of age-matched Tg mice were treated with the carrier vehicle only. Age-matched Tg mice served as negative control indicating that plaque was present, but no drug was administered.

All animals were sacrificed beginning 1, 3 and 10 h after the final dose. Fresh brains of the animals were removed, bisected, and positioned in o-chlorotoluene (OCT). The brains were immersed into 2-methylbutane, pre-cooled to 150° C. with liquid nitrogen. The brains were cut into 20 μm thick sections at a temperature of −20° C. Brain sections were collected onto poly-L-lysine-coated glass microscopic slide and treated with (1 drop) of 75%, by volume (v/v), glycerin in poly(butene-1-sulfone)(PBS). Each section was thawed briefly, covered with a coverslip, and examined immediately under a Zeiss LSM510 scanning laser microscope ($\lambda_{ex}$ is 488 nm; $\lambda_{em}$ is greater than 520 nm) to determine the extent and distribution of compound-associated fluorescence.

The section adjacent to each compound-treated section of the brain was stained with thioflavin S (Sigma Chemicals, Milwaukee, Wis., U.S.A.). Sections stained with thioflavin S served as a positive control for identifying plaque. The distribution of compound-associated fluorescence was compared with the distribution of thioflavin S-stained section in order to confirm whether the compound bound plaque.

All sections were examined 1 h later to assess artifactual drug diffusion within thawed sections over time.

Adjacent brain sections of compound-treated mice displayed intense drug-related fluorescence ($\lambda_{ex}$ is 365 nm; $\lambda_{em}$ is 400 nm) in areas of plaque formation. The data confirm that the quinolinehydrazone compound is brain penetrable and preferentially binds to human β-amyloid containing plaques.

All brain sections obtained from Tg mice receiving the quinolinehydrazone compound demonstrated marked plaque burden when compared with sections stained by thioflavin S.

EXAMPLE 2

Dose-Dependent Pharmacokinetics in Plasma and Brain Concentrations

Dose-proportionality characteristics were assessed by measuring the maximum concentration ($C_{max}$) for plasma and brain concentrations after oral dosing of normal mice. The mice were treated with six, individual, oral doses increased proportionally from 50 to 3,200 μmole/kg. Plasma and brain concentrations were measured by HPLC at 0.5 to 24 hours. The test results showed that $C_{max}$ for plasma and brain increases proportionally from 400 to 3,200 μmol/kg without evidence of absorption saturation.

EXAMPLE 3

In Vivo Determination of Plasma and Brain Exposure

Plasma and brain exposure were assessed by measuring area under the curve (AUC) after oral dosing of normal mice. All mice were treated with six, individual, oral doses increased proportionally from 50 to 3,200 μmole/kg. The data showed that plasma exposure increased proportionally from 421 to 1,472 μmol/kg, but showed evidence of saturation at 3,024 μmol/kg. Brain exposure increased more rapidly in the range between from 421 to 1,472 μmol/kg, but showed a similar saturation phenomenon at higher doses.

The brain to plasma ratios were calculated and reported below.

| Dose μmole/kg | Plasma AUC (0 to last) | Brain AUC (0 to last) | B/P Ratio AUC |
|---|---|---|---|
| 51 | 0.991 | 5.22 | 5.3 |
| 208 | 17 | 54.7 | 3.2 |
| 421 | 75.2 | 187 | 2.5 |
| 831 | 152 | 863 | 5.7 |
| 1472 | 262 | 1490 | 5.7 |
| 3024 | 235 | 1714 | 7.3 |

The results summarized in the above table evidence good penetration of the compound to the brain tissue. As shown above, brain levels average 5 times greater than plasma levels over the dose range tested.

The terminal half-life of compound in the brain was measured to determine the dosing frequency for 10-day tolerance studies. For the three highest doses, brain terminal half-life ranged from 5–7 h.

EXAMPLE 4

Postmortem Staining of Amyloid Plaque

Brains from 12–14 month-old Tg mice were frozen and sectioned at −20° C. Each section was fixed in ice cold methanol (Aldrich Chemical Co., Milwaukee, Wis.) for 10 minutes, rinsed in buffer and incubated in 4-methyl-7-methoxy-2-(4-quinolylmethylenehydrazino)quinoline for 90 minutes at room temperature. Drug concentrations ranging from 0.01 M to 10 M effectively demonstrated amyloid plaque in brains of Tg mice, but not in brains of transgene-free mice. Fluorescence intensity in Tg mouse amyloid decreased with drug concentration. Staining of the adjacent brains sections with thioflavin S confirmed that the compound fluorescence does localize in amyloid plaques. The transgene mouse brains were confirmed to be plaque-free.

EXAMPLE 5

Determination of In Vitro Antioxidant Effect using Neuronal Cytoprotection Model The 4-methyl-7-methoxy-2-(4-quinolylmethylenehydrazino)quinoline was dissolved in 100×stock of aqueous Locke's buffer to obtain concentrations of 1, 3, 10, 30, and 100 μM solution. Neuronal cells were incubated in each compound solution with and without ferrous ammonium sulfate (200 μm) for 3 hours. High concentration supernatant was obtained from each sample. The samples were analyzed under liquid chromatography/mass spectrometry (LC/MS). The quinoline demonstrated antioxidant properties.

EXAMPLE 6

Determination of In Vitro Antioxidant Effect using Ferrous Ammonium Sulfate (FAS)-Induced Oxidative Toxicity Model The 4-methyl-7-methoxy-2-(4-quinolylmethylenehydrazino)quinoline was tested in a primary neuronal model of FAS-induced lipid peroxidation toxicity. The compound was treated in two manners. In one manner, the compound was solubilized as 100×stock in 100% dimethyl sulfoxide (DMSO) to afford panel A. In another manner, the compound was solubilized in aqueous Locke's buffer to give panel B.

The data showed that the concentration of the drug dependently inhibited 200 μM FAS toxicity after 3 hours from 0.3–10 MM and showed close to or complete neuronal protection at 10 μM when cell viability was measured using $^{14}$C-AIB uptake or lactic dehydrogenase (LDH) release. Concentrations above 10 μM (30 and 100 μM) in 1% DMSO experiments revealed inherent drug toxicity and no neuronal protection against FAS in panel A. In the aqueous preparation of the compound there was much less drug toxicity at 30 μM and considerable neuronal protection at 30 and 100 μM, respectively. Brightfield photographs revealed the cell morphology of the 10 μM+FAS cells to be no different than cells treated with no drug and no FAS (control cells).

The data suggested that antioxidant properties of the compound could enable the compound for having a dual pharmacology. Along with its putative ability to inhibit plaque formation in Alzheimer's disease the compound also could inhibit any oxidative neuronal damage associated with beta-amyloid.

The foregoing are intended to illustrate the invention and are not meant to limit the scope of the invention, which is defined in the appended claims.

What is claimed is:

1. A method for chemically tagging the aggregation of amyloid fibrils comprising the steps of:
   (a) administering a compound of the following formula to a mammal or contacting said compound with a fluid or tissue sample taken from the mammal, the compound having the following formula:

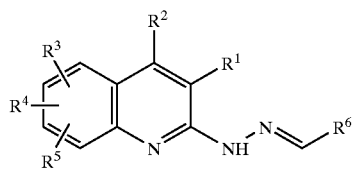

(I)

or a pharmaceutically acceptable salt, ester, solvate, or prodrug thereof, wherein:
$R^1$, $R^2$, $R^3$, $R^4$, and $R^5$ are independently selected from the group consisting of hydrogen, alkyl, cycloalkyl, aryl, triflouromethyl, trifluoromethylether, halo, and a group of the formula —$OR^7$, wherein $R^7$ is alkyl or aryl; and $R^6$ is a benzopyridinyl group optionally substituted with one to three substituents selected from the group consisting of hydrogen, alkyl, cycloalkyl, aryl, triflouromethyl, trifluoromethylether, halo, and a group of the formula —$OR^7$, wherein $R^7$ is alkyl or aryl;

wherein said alkyl groups at each occurrence are optionally substituted with alkoxy, aryl, or halo; said aryl groups at each occurrence are optionally substituted with alkyl, alkoxy, or halo; and one or more atoms in the compound of formula (I) optionally is replaced with a radiolabeled atom; and (b) allowing the compound to associate with the amyloid fibrils.

2. The method of claimed 1 wherein the radiolabeled atom is selected from the group consisting of $^3$H, $^{131}$I, $^{125}$I, $^{76}$Br, $^{18}$F, $^{19}$F, $^{15}$O, and $^{11}$C.

3. The method of claim 1 wherein $R^1$, $R^2$, $R^3$, $R^4$, and $R^5$ are each independently selected from the group consisting of hydrogen, methyl, ethyl, n-propyl, isopropyl, n-butyl, sec-butyl, t-butyl, n-pentyl, t-pentyl, n-hexyl, methoxy, ethoxy, isopropoxy, sec-butoxy, t-butoxy, phenyl, benzyl, triflouromethyl, trifluoromethylether, and halo.

4. The method of claim 1 wherein the benzopyridinyl group for $R^6$ is quinolyl or isoquinolyl.

5. The method of claim 1 wherein the compound of formula (I) in step (a) is incorporated in a pharmaceutically acceptable carrier.

6. The method of claim 1 wherein the compound of formula (I) in step (a) is selected from the group consisting of:
   4-methyl-7-methoxy-2-(4-quinolylmethylenehydrazino) quinoline;
   4-ethyl-7-methoxy-2-(4-quinolylmethylenehydrazino) quinoline;
   4-ethyl-7-ethoxy-2-(4-quinolylmethylenehydrazino) quinoline;
   4-methyl-7-ethoxy-2-(4-quinolylmethylenehydrazino) quinoline;
   4-ethyl-7-ethoxy-2-(3-quinolylmethylenehydrazino) quinoline;
   4-ethyl-7-methoxy-2-(3-quinolylmethylenehydrazino) quinoline; and
   4-methyl-7-methoxy-2-(3-quinolylmethylenehydrazino) quinoline.

7. The method of claim 1 wherein the compound of formula (I) is 4-methyl-7-methoxy-2-(4-quinolylmethylenehydrazino)quinoline.

8. A method for detecting an aggregation of amyloid fibrils comprising the steps of:
   (a) administering a compound of the following formula to a mammal or contacting said compound with a fluid or tissue sample taken from the mammal, the compound having the following formula:

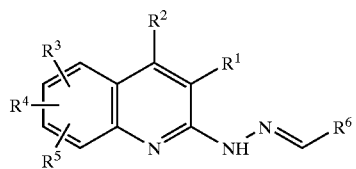

(I)

or a pharmaceutically acceptable salt, ester, solvate, or prodrug thereof, wherein:
$R^1$, $R^2$, $R^3$, $R^4$, and $R^5$ are independently selected from the group consisting of hydrogen, alkyl, cycloalkyl, aryl, triflouromethyl, trifluoromethylether, halo, and a group of the formula —$OR^7$, wherein $R^7$ is alkyl or aryl; and $R^6$ is a benzopyridinyl group optionally substituted with one to three substituents selected from the group consisting of hydrogen, alkyl, cycloalkyl, aryl, triflouromethyl, trifluoromethylether, halo, and a group of the formula —$OR^7$, wherein $R^7$ is alkyl or aryl;

wherein said alkyl groups at each occurrence are optionally substituted with alkoxy, aryl, or halo; said aryl groups at each occurrence are optionally substituted with alkyl, alkoxy, or halo; and at least one atom in the compound is replaced with a radiolabeled atom;

(b) allowing the compound to associate with the amyloid fibrils to provide a labeled deposit; and
   (c) detecting the amount and location of the labeled deposit.

9. The method of claim 8 comprising the steps of detecting the labeled deposit by gamma imaging, magnetic resonance imaging, or magnetic resonance spectroscopy.

10. The method of claim 8 comprising the step of (d) evaluating or assessing the data obtained in step (c) in an individual and optionally comparing the data with analogous data obtained from a normal human or mammal to identify, assess, or diagnose the medical condition of the individual.

11. The method of claim 10 comprising assessing the condition of an individual undergoing treatment for a condition characterized by the aggregation of amyloid fibrils.

12. The method of claim 11 wherein the condition is selected from the group consisting of Alzheimer's disease, Down syndrome, Type 2 diabetes mellitus, hereditary cerebral hemorrhage amyloidosis, amyloid A, secondary amyloidosis, familial Mediterranean fever, familial amyloid nephropathy with urticaria and deafness, amyloid lambda L-chain or amyloid kappa L-chain, A beta 2M, ATTR, familial amyloid cardiomyopathy, isolated cardiac amyloid, AIAPP or amylin insulinoa, atrial naturetic factor, procalcitonin, gelsolin, crytatin C, AApo-A-I, AApo-A-II, fibrinogen-associated amyloid; and Asor or Pr P-27 or in cases of persons who are homozygous for the apolipoprotein E4 allele, and the condition associated with homozygosity for the apolipoprotein E4 allele; and the treatment comprises administering an active agent selected from the group consisting of doxorubicin, galantamine, tacrine, selegiline, physostigmine, revistigmin, donepizil, metrifonate, milameline, xanomeline, saeluzole, acetyl L carnitine, idebenone, ENA 713, memric, quetiapine neurestrol and neuromidal.

13. A method for detecting a condition in an individual characterized by aggregation of amyloid fibrils comprising the steps of:
(a) administering a compound of the following formula to a mammal or contacting said compound with a fluid or tissue sample taken from the mammal, the compound having the following formula:

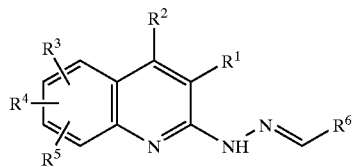

or a pharmaceutically acceptable salt, ester, solvate, or prodrug thereof, wherein:
$R^1$, $R^2$, $R^3$, $R^4$, and $R^5$ are independently selected from the group consisting of hydrogen, alkyl, cycloalkyl, aryl, triflouromethyl, trifluoromethylether, halo, and a group of the formula —$OR^7$, wherein $R^7$ is alkyl or aryl; and
$R^6$ is a benzopyridinyl group optionally substituted with one to three substituents selected from the group consisting of hydrogen, alkyl, cycloalkyl, aryl, triflouromethyl, trifluoromethylether, halo, and a group of the formula —$OR^7$, wherein $R^7$ is alkyl or aryl;
wherein said alkyl groups at each occurrence are optionally substituted with alkoxy, aryl, or halo; and said aryl groups at each occurrence are optionally substituted with alkyl, alkoxy, or halo;
at least one atom of the compound of formula (I) being replaced with a radiolabeled atom;
(b) allowing the compound to associate with the amyloid fibrils to provide a labeled deposit; and
(c) detecting the condition by detecting the amount and location of the labeled deposit.

14. The method of claim 13 wherein the compound of formula (I) is incorporated in a pharmaceutically acceptable carrier.

15. The method of claim 13 wherein the condition is selected from the group consisting of Alzheimer's disease, Down syndrome, Type 2 diabetes mellitus, hereditary cerebral hemorrhage amyloidosis, amyloid A, secondary amyloidosis, familial mediterranean fever, familial amyloid nephropathy with urticaria and deafness, amyloid lambda L-chain or amyloid kappa L-chain, A beta 2M, ATTR, familial amyloid cardiomyopathy, isolated cardiac amyloid, AIAPP or amylin insulinoa, atrial naturetic factor, procalcitonin, gelsolin, crytatin C, AApo-A-I, AApo-A-II, fibrinogen-associated amyloid; and Asor or Pr P-27 or in cases of persons who are homozygous for the apolipoprotein E4 allele, and the condition associated with homozygosity for the apolipoprotein E4 allele.

16. The method of claim 13 wherein the condition is selected from the group consisting of Dutch hereditary cerebral hemorrhage amyloidosis amyloid A, Muckle-wells syndrome, idiopathic-associated amyloid lambda L-chain, myeloma-associated amyloid lambda L-chain, macroglobulinemia-associated amyloid lambda L-chain, idiopathic-associated amyloid kappa L-chain, myeloma-associated amyloid kappa L-chain, macroglobulinemia-associated amyloid kappa L-chain, Portuguese familial amyloid polyneuropathy, Japanese familial amyloid polyneuropathy, Swedish familial amyloid polyneuropathy, Danish familial amyloid cardiomyopathy, systemic senile amyloidosises, isolated atrial amyloid, medullary carcinoma of the thyroid, Finnish familial amyloidosis, Icelandic hereditary cerebral hemorrhage with amyloidosis, scrapie, Cruetzfeld-Jacob disease, Gertsmann-Straussler-Scheinker syndrome, and bovine spongiform encephalitis.

17. A method for staining amyloid fibrils comprising the steps of:
(a) providing a compound of the formula:

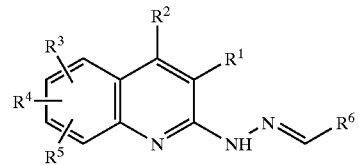

or a pharmaceutically acceptable salt, ester, solvate, or prodrug thereof, wherein:
$R^1$, $R^2$, $R^3$, $R^4$, and $R^5$ are independently selected from the group consisting of hydrogen, alkyl, cycloalkyl, aryl, triflouromethyl, trifluoromethylether, halo, and a group of the formula —$OR^7$, wherein $R^7$ is alkyl or aryl; and
$R^6$ is a benzopyridinyl group optionally substituted with one to three substituents selected from the group consisting of hydrogen, alkyl, cycloalkyl, aryl, triflouromethyl, trifluoromethylether, halo, and a group of the formula —$OR^7$, wherein $R^7$ is alkyl or aryl;
wherein said alkyl groups at each occurrence are optionally substituted with alkoxy, aryl, or halo; said aryl groups at each occurrence are optionally substituted with alkyl, alkoxy, or halo; and one or more atoms in the compound of formula (I) is replaced with a radiolabeled atom;

(b) applying the compound to a sample containing amyloid fibrils to form a labeled deposit; and (c) detecting the labeled deposit.

18. The method of claim 17 wherein the compound is incorporated in a pharmaceutically acceptable carrier.

19. A method for detecting amyloid deposits in biopsy or postmortem human or animal tissue comprising the steps of:

(a) incubating formalin-fixed biopsy or postmortem human or animal tissue with a solution of a compound of the formula:

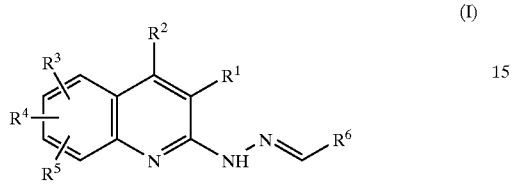

(I)

or a pharmaceutically acceptable salt, ester, solvate or prodrug thereof, wherein:

$R^1$, $R^2$, $R^3$, $R^4$, and $R^5$ are independently selected from the group consisting of hydrogen, alkyl, cycloalkyl, aryl, triflouromethyl, trifluoromethylether, halo, and a group of the formula —$OR^7$, wherein $R^7$ is alkyl or aryl; and $R^6$ is a benzopyridinyl group optionally substituted with one to three substituents selected from the group consisting of hydrogen, alkyl, cycloalkyl, aryl, triflouromethyl, trifluoromethylether, halo, and a group of the formula —$OR^7$, wherein $R^7$ is alkyl or aryl;

wherein said alkyl groups at each occurrence are optionally substituted with alkoxy, aryl, or halo; said aryl groups at each occurrence are optionally substituted with alkyl, alkoxy, or halo; and one or more atoms in the compound of formula (I) is replaced with a radiolabeled atom; to provide a labeled deposit; and (b) detecting the labeled deposit.

* * * * *

UNITED STATES PATENT AND TRADEMARK OFFICE
CERTIFICATE OF CORRECTION

PATENT NO. : 6,589,504 B1
DATED : July 8, 2003
INVENTOR(S) : Raub et al.

It is certified that error appears in the above-identified patent and that said Letters Patent is hereby corrected as shown below:

Column 17,
Line 59, after "The method of," please delete "claimed 1" and insert -- claim 1 -- in its place.
Line 60, after "consisting of $^3$H, $^{131}$I," please delete "$^{125}$I, $^{76}$Br" and insert -- $^{125}$I, $^{123}$I, $^{76}$Br -- in its place.

Column 19,
Line 1, after "The method of," please delete "claim 8 comprising" and insert -- claim 8 further comprising -- in its place.

Signed and Sealed this

Eighteenth Day of November, 2003

JAMES E. ROGAN
*Director of the United States Patent and Trademark Office*